United States Patent
Yamamoto

(10) Patent No.: US 7,160,375 B2
(45) Date of Patent: Jan. 9, 2007

(54) AQUEOUS GLITTERING COLOR MATERIAL COMPOSITION

(75) Inventor: Yuki Yamamoto, Yamatokoriyama (JP)

(73) Assignee: Sakura Color Products Corporation, Osaka-fu (JP)

( * ) Notice: Subject to any disclaimer, the term of this patent is extended or adjusted under 35 U.S.C. 154(b) by 3 days.

(21) Appl. No.: 10/503,688

(22) PCT Filed: Feb. 4, 2003

(86) PCT No.: PCT/JP03/01145

§ 371 (c)(1),
(2), (4) Date: Aug. 4, 2004

(87) PCT Pub. No.: WO03/066745

PCT Pub. Date: Aug. 14, 2003

(65) Prior Publication Data

US 2005/0148685 A1    Jul. 7, 2005

(30) Foreign Application Priority Data

Feb. 5, 2002   (JP) ............... 2002-027690

(51) Int. Cl.
C09D 11/16   (2006.01)
C09C 1/62    (2006.01)
(52) U.S. Cl. .............. 106/31.6; 106/403; 106/404; 106/415; 106/416; 106/489; 106/490
(58) Field of Classification Search .............. 106/31.6, 106/403, 404, 415, 416, 489, 490
See application file for complete search history.

(56) References Cited

U.S. PATENT DOCUMENTS 6,488,757 B1 * 12/2002 Glausch .............. 106/415
6,544,323 B1 * 4/2003 An ..................... 106/31.68
6,663,704 B1 * 12/2003 Spencer et al. ......... 106/31.9
2002/0128350 A1   9/2002 Yoshimura et al.

FOREIGN PATENT DOCUMENTS

| EP | 0 679 700 | 11/1995 |
| EP | 1 038 931 | 9/2000 |
| EP | 1 111 018 | 6/2001 |
| JP | 7-70467 | 3/1995 |
| JP | 9-188830 | 7/1997 |
| JP | 10-81837 | 3/1998 |
| JP | 10-259317 | 9/1998 |
| JP | 2001-164150 | 6/2001 |
| JP | 2001-192588 | 7/2001 |
| JP | 2001-192597 | 7/2001 |
| JP | 2001-192598 | 7/2001 |
| JP | 2001-262014 | 9/2001 |
| JP | 2001-335731 | 12/2001 |

* cited by examiner

Primary Examiner—J. A. Lorengo
Assistant Examiner—Veronica Faison-Gee
(74) Attorney, Agent, or Firm—Hamre, Schumann, Mueller & Larson, PC

(57) ABSTRACT

An aqueous glittering color material composition of the present invention is an aqueous glittering color material composition comprising a glittering pigment having a water repellent particle surface and it includes the following ingredients. The aqueous glittering color material composition of the present invention is used for an ink for writing instruments, for cosmetics, and the like.
(a) As said glittering pigment, a metal coated glass flake pigment having a particle surface with water repellent treatment with a titanate or a silane coupling agent.
(b) A colorant, and
(c) A fixing resin.

33 Claims, 3 Drawing Sheets

AQUEOUS GLITTERING COLOR MATERIAL COMPOSITION

BACKGROUND OF THE INVENTION

Field of the Invention

The present invention relates to an aqueous glittering color material composition which can be used for an ink for writing instruments, a marking ink, a paint, a stamp ink, a stencil ink, as well as cosmetics for makeup, coating materials, and the like. In particular, the present invention relates to an ink composition, and specifically relates to an aqueous ink composition suitable for an ink for various kinds of writing instruments such as ballpoint pens and writing instruments whose pen tip is made of a fiber bundle and in further detail, the present invention relates to an aqueous glittering ink composition capable of creating a written mark which glitters like a star dust in various colors in which glittering pigment particles are scattered.

Japanese Unexamined Patent Publication No. 2001-262014 discloses a glittering ink composition which comprises glittering pigments including glass flake pigments which are coated with a metal, a water-soluble resin, a water-soluble organic solvent, and water. Said ink lets a light metallically reflect on written marks since a pigment particle of glittering pigments has a smooth metal surface, thereby capable of creating written marks which glitter like a star dust. And when writing with said ink with coloring pigments contained in said ingredients, coloring effect by coloring pigments is obtained while glittering by glittering pigments having relatively larger particle diameter than particle diameter of coloring pigments and glittery written marks in various color tone are obtained.

However, in the case of said ink in which colorants including coloring pigment is contained, since written marks include colorants including coloring pigments other than glittering pigments, for example, as shown in schematic diagram of an example of a written mark in FIG. 2, the larger the content of a coloring pigment in an ink, the more satisfactory coloring effect realized by pigment particle 2 of coloring pigment is obtained in written mark 1, while on the other hand, since the degree of covering pigment particle 3 of a glittering pigment by pigment particle 2 of coloring pigment increases, metal reflection by light 4 is hard to occur on a smooth surface of pigment particle 3 of said glittering pigments, and as a result, such written mark 1 is realized which is thick as a whole but which has lower glittering property. On the other hard, the smaller the content of a coloring pigment in an ink, for example, as shown in schematic diagram of an example of a written mark in FIG. 3, since the degree of covering pigment particle 3 of a glittering pigment by pigment particle 2 of said coloring pigment decreases, metal reflection by light 4 is easy to occur on a smooth surface of pigment particle 3 of said glittering pigments thereby improving glittering property, however, at the same time, since the content of coloring pigment decreases, coloring effect by said coloring pigment lowers and the written mark has a glittering property but light.

The object of the present invention is to provide an aqueous glittering color material composition, in particular, an aqueous glittering ink composition or glittering cosmetics capable of improving coloring effect by a colorant and glittering property by a glittering pigment in a written mark as a whole at the same time when compared with conventional inks as mentioned above.

DISCLOSURE OF THE INVENTION

As a result of intensive studies to achieve said objective, the present invention has adopted an aqueous glittering color material composition comprising a glittering pigment having a water repellent particle surface.

By this, when writing or coating by using a composition of the present invention, unlike embodiments of conventional examples of a written mark or a coated film as shown in FIGS. 2 and 3, as shown in FIG. 1 for example, in pigment particle 3 of a glittering pigment, water and the like included in an aqueous color material composition or a pigment dispersion are rejected on a water repellent particle surface 3a and a surface of pigment particle 3 of a glittering pigment is exposed. Accordingly, a reflection surface of light 4 is saved, which increases glittering property. In particular, as shown in FIG. 1, when a colorant such as a coloring pigment or a dye is included in said composition, for example, pigment particle 2 of said coloring pigment is easily removed from a particle surface of pigment particle 3 together with said water and the like, thereby capable of preventing formation of a written mark or a coated film in which a colorant such as a coloring pigment and the like covers a particle surface of pigment particle 3 of a glittering pigment.

In addition, since pigment particles 2 of a coloring pigment removed from a particle surface of pigment particle 3 of a glittering pigment thus far are scattered around pigment particle 3 of said glittering pigment, for example, its written mark or a coated film has improved glittering property by a glittering pigment in a written mark or a coated film as a whole and in particular, when a colorant is included, such a written mark or a coated film can be obtained in which both coloring effect by a colorant and glittering property by a glittering pigment are improved at the same time. For information, the present invention is not limited to a written mark model shown in said FIG. 3.

For information, although said glittering pigments are not limited, glittering pigments whose median diameter of said glittering pigment particles is at least 10 μm are preferable and glass flake pigments having a structure in which a metal is coated on glass flakes are also preferable. In addition, as preferable said glittering pigments, pigments having a particle surface with water repellent treatment, in particular, an aqueous glittering color material composition comprising glittering pigments with water repellent treatment by water repellent agents are preferable.

Although said water repellent agents are not limited, coupling agents are preferable, and in particular, as said coupling agents, titanate coupling agents or silane coupling agents are preferable.

Therefore, as preferable said aqueous glittering color material composition, a composition comprising a colorant, a solvent, a glittering pigment with a water repellent particle surface, in particular, a glittering pigment with a water repellent particle surface which rejects said colorant.

Although a composition of the present invention is not limited, it is preferably used particularly as an aqueous glittering ink or aqueous glittering cosmetics which are coated on a skin or a flesh like make-ups.

In particular, it is assumed that said coloring material composition comprising a glittering pigment having a water repellent particle surface and a median diameter of said particle of at least 10 μm has particularly good glittering feeling on exposed surface of a glittering pigment and concentration of a colorant and the like which was rejected from a glittering pigment, and actually a written mark or a coated film in which coloring effect by a colorant on a written mark or a coated film as a whole is strong and at the same time a written mark or a coated film which has improved glittering property can be obtained.

Figure 1:
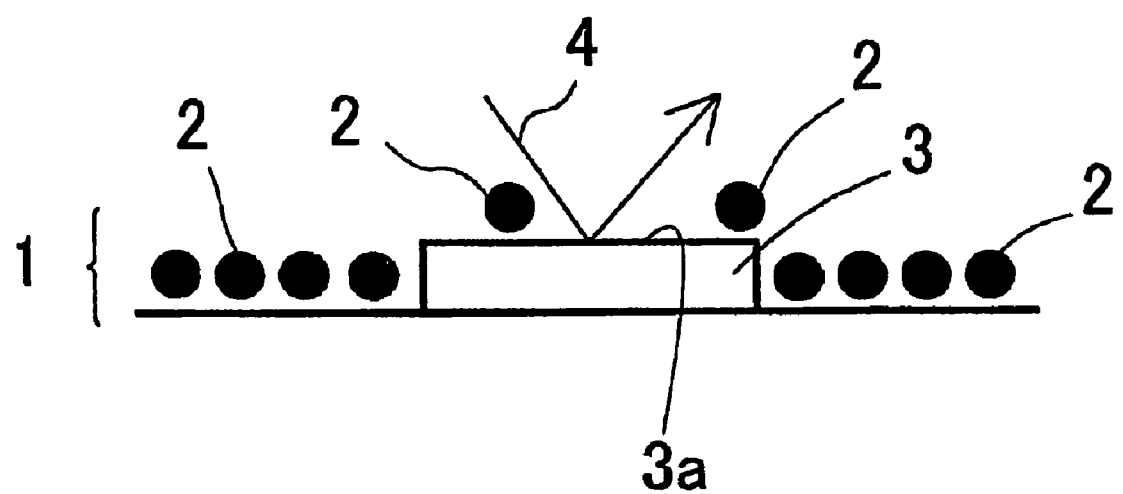
FIG. 1 is a schematic diagram showing an example of a written mark or a coated film which was formed by a glittering pigment having a water repellent particle surface using a composition related to the present invention.
Figure 2:
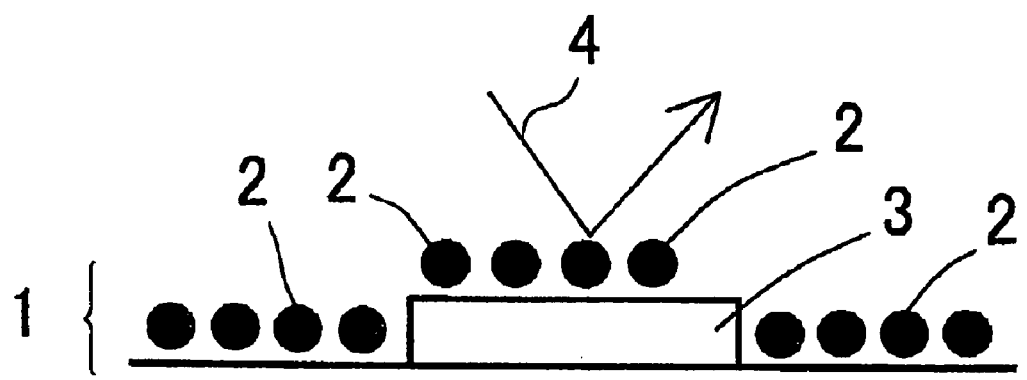
FIG. 2 is a schematic diagram showing a state in which a pigment particle of a coloring pigment covers a surface of a pigment particle of a glittering pigment using a composition comprising a glittering pigment having no water repellent particle surface.
Figure 3:
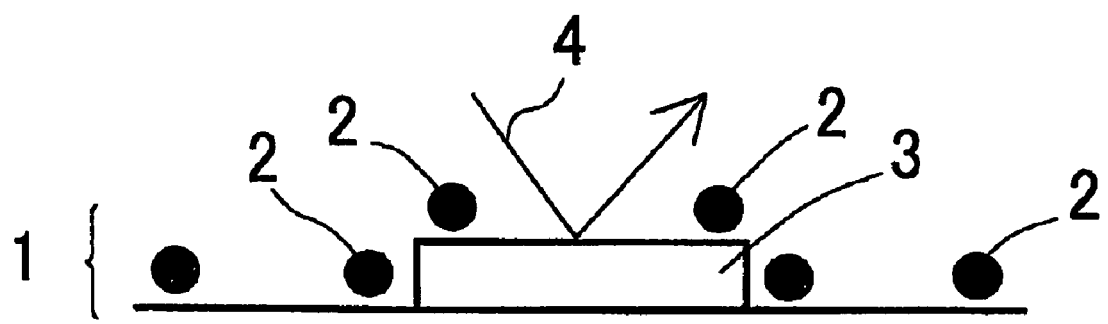
FIG. 3 is a schematic diagram showing a state in which a pigment particle of a coloring pigment covers almost no surface of a pigment particle of a glittering pigment using a composition comprising a glittering pigment having no water repellent particle surface.

DESCRIPTION OF THE PREFERRED EMBODIMENT (Glittering Pigments)

Glittering pigments used in the present invention are not specially limited and any glittering pigments can be used as long us those having a water repellent particle surface. In particular, it is important that in the present invention, glittering pigment having a water repellent particle surface which rejects a colorant is included in an aqueous color material composition such as an ink composition, and the like. For example, in the case of a color material composition such as an aqueous ink and the like including a glittering pigment having a water repellent particle surface together with a water soluble dye, a water soluble pigment, a colorant including a water dispersible pigment and the like, water, and an aqueous solvent including water soluble organic solvent, when writing, said colorant is easily rejected from a particle surface of a water repellent glittering pigment in a written mark, which can exclude a colorant covering a particle surface of a glittering pigment quickly, thereby capable of creating a written mark or a coated film in which a colorant gathers around a particle of a glittering pigment.

A glittering pigment having a water repellent particle surface is obtained by, for example, applying water repellent treatment to a particle surface of a glittering pigment. Although specific examples of water repellent treatment are not particularly limited, it is preferable to use a water repellent agent. For example, to make a particle surface of a metal (which includes alloy) or a metal oxide such as said glittering pigment, in particular, to make a particle surface of a metal (which includes alloy) water repellent, it is preferable to use a water repellent agent such as coupling agent and the like for water repellent treatment. As coupling agents, titanate or silane coupling agents are preferably used. As titanate coupling agents, for example, trade names "KR ET", "KR 44", "KR TTS", "KR 38S", "KR 138" and the like manufactured by Ajinomoto Fine Techno Co. Inc. are used. As aluminate coupling agents, for example, a trade name "A1-M" manufactured by Ajinomoto Fine Techno Co Inc is used. As silane coupling agents, trade names "KBM 403", "KBM 603", and "KBM 903" and the like manufactured by Shin-Etsu Chemical Co. Ltd are used.

The preferable content range of a water repellent agent, in particular, the preferable range of a coupling agent is at least 0.1% by weight with respect to a glittering pigment. When the content of a water repellent agent is less than 0.1% by weight, the satisfactory effect of water repellency is hard to be obtained.

As said glittering pigment, for example, pigments having a metal reflection surface (a smooth metal reflection surface, preferably a mirror reflection surface) in a pigment particle surface or inside of a particle and composed of a single or multiple layered particle having a particle surface which develops glittery glitter by a light reflection can be used. In order to show excellent glittering property, it is desirable that this pigment particle is a glittering pigment composed of a single layer or multiple layers of a scaly type, flaky type, thin film type, or plate type. In particular, a glittering particle having a smooth surface in which an incident light totally reflects is preferable. Although metals which compose said metal reflection surface are not specifically limited, metal unit or metal alloy with light reflectance of not less than 0.5 is preferable, and silver (reflectance; 0.94), aluminum (reflectance; 0.83), gold (reflectance; 0.80), and nickel (reflectance; 0.63) and the like are exemplified. In addition, as glittering pigments composed particularly of a single layer or multiple layers of a scaly type, flaky type, thin film type, or plate type, glittering pigments having a median diameter of at least 10 µm, in particular, glittering pigments selected from metal coated glass flake pigments, metal coated inorganic pigments, and aluminum pigments are preferable. When a median diameter of this glittering pigment particle is less than 10 µm, even though water repellent treatment is applied on a pigment particle surface with a water repellent agent, glittering property appearing on a written mark or a coated film lowers. For information, in the case of a color material composition, in particular, in the case of an ink which comprises a glittering pigment including a scaly glittering pigment and the like whose median diameter is at least 25 µm, preferably 30 µm, excellent glittering property is shown in a written mark or a coated film.

Specific examples of glittering pigments (glittering particles) used in the present invention include metal coated glass flake pigments, metal coated inorganic pigments, metal oxide coated inorganic pigments, aluminum pigments, metal foils, films deposited with metals, and metal deposited films (for example, metal deposited films obtained by stripping off metal deposited layers which were deposited on films). Here, metal glass flake pigments are defined to be the pigments composed of a structure in which a flaky glass is coated by a metal (alloy). Also, metal glass flake pigments are defined as genetic terms for inorganic pigments coated with a metal (alloy). Also, inorganic pigments coated with metal oxides (for example, metal pigments such as aluminum pigments coated with metal oxides) can be used.

One example of metal coated glass flake pigments includes glass flake particles in which flaky glass is coated with a metal by electroless deposition. For example, each gold, green, and red of trade names "Metashine REFSX-2015PS", "Metashine REFSX-2025PS", and "Metashine REFSX-2040PS" coated with silver manufactured by Toyo Aluminium KK, trade names "Metashine RCFSX-1040RS" and "Metashine RCFSX-1040RC" coated with titanium manufactured by Toyo Aluminium KK can be exemplified. In addition, as glass flake particles, such glass flake particles as coated with metals by a pattering method can be used. For example, trade names "Crystal color GF2125", "Crystal color GF2125-M", "Crystal color GF2140", and "Crystal color GF2140-M" which are coated with silver manufactured by Toyo Aluminium KK are exemplified. Also, trade names "Crystal color GF2525", "Crystal color GF2525-M", "Crystal color GF2540", and "Crystal color GF2540-M" which are coated with nickel chrome molybdenum manufactured by Toyo Aluminium KK are exemplified. Also, trade names "Crystal color GF250" coated with bronze, "Crystal color GF1345" coated with silver alloy, and "Crystal color GF1445" coated with titanium manufactured by Toyo Aluminium KK are exemplified.

To cite one example as metal coated inorganic pigments or metal oxide coated inorganic pigments, aluminum coated with iron oxide (III) can be used. For example, trade names "Paliocrom Gold L2000", "Paliocrom Gold L2002", "Paliocrom Gold L2020", "Paliocrom Gold L2022", "Paliocrom Gold L2025", and "Paliocrom Orange L2800" manufactured by BASF Japan are exemplified. In addition, mica coated with iron oxide (III) can be used. For example, trade names "Paliocrom Red Gold L2500" and "Paliocrom Red L4000" manufactured by BASF Japan are exemplified. In addition, mica like iron oxide (III) coated with aluminum-manganese can be used. For example, trade names "Paliocrom Copper L3000" and "Paliocrom Copper L3001" manufactured by BASF Japan are exemplified. Further, mica coated with reduced titanium dioxide can be used. For example, "Paliocrom Blue Silver L6000" and "Paliocrom Blue Silver L6001" manufactured by BASF Japan like are exemplified.

In addition, in the present invention, simple substance of a metal including aluminum powder and the like can also be used. Also, flakes or thin slices of deposited aluminum film in which aluminum is deposited on a resin film, thereby stripping off or unifying resin films can also be used. As aluminum powders, trade name "WXM U75C" (median diameter: 13 μm) manufactured by Toyo Aluminium KK, trade name "WXM 5452" (median diameter: 18 μm) manufactured by said company, trade name "WXM 1440" (median diameter: 30 μm) manufactured by said company, trade name "WXM 1415" (median diameter: 50 μm) manufactured by said company can be exemplified. In particular, in the case of aluminum powder, trade name "WXM 1440" (median diameter: 30 μm) manufactured by said company, trade name "WXM 1415" (median diameter: 50 μm) manufactured by said company can preferably be used in which median diameter of a particle exceeds 25 μm and not less than 30 μm. These can be used either alone or in combinations of two or more of them.

It is preferable that the content of glittering pigments as mentioned above (in particular, scaly glittering particles), and preferably, the content of glittering pigments whose median diameter of a pigment particle is at least 10 μm is 0.01 to 40% by weight with respect to the total amount of the color material composition, in particular, with respect to the total amount of the ink composition.

When the content of said glittering pigment is less than 0.01% by weight with respect to the total amount of the aqueous color material composition such as all aqueous ink composition and the like, even though a colorant is rejected from a surface of a glittering pigment particle in a written mark or a coated film, glittering property is hard to be shown in a satisfactory manner. In addition, when the content of said glittering pigment exceeds 40% by weight with respect to the total amount of said color material composition, viscosity becomes too high in particular as an ink and fluidity lowers and writing performance deteriorates. The optimal content of a glittering pigment is 0.5 to 30% by weight. If the content is within this range, satisfactory glittering property can be realized in a required minimum content partly because a colorant is rejected from a particle surface of a glittering pigment.

(Colorant)

As a colorant used in the present invention, it is important that such a colorant should be used as neither react with said glittering pigment nor influence glittering property. Further, as a colorant, it is preferable that a colorant is aqueous and has high solubility and dispersibility to an aqueous color material composition such as an ink and the like.

Specific examples include water-soluble dyes such as acid dyes, direct dyes and basic dyes, inorganic pigments such as carbon black and titanium oxide, organic pigments such as copper phthalocyanine pigments, threne pigments, azo pigments, quinacridon pigments, anthraquinone pigments, dioxane pigments, indigo pigments, thioindigo pigments, perinone pigments, perylene pigments, indolenone pigments and azomethine pigments and the like, and fluorescent pigments, colored resin emulsions and the like can be mentioned. These also may be used in the form of pigment dispersions. In short, in the present invention, colorants selected for example from water soluble dyes, water soluble pigments, and water soluble pigment dispersions. Further, the present invention can use one species of a colorant or can use two or more species of colorants in combinations. Furthermore, they can be mixed with opacifying pigments including a variety of inorganic or organic white pigments such as titanium oxide, alkylene bismelamine derivatives, plastic pigments (synthetic resin particle pigments) with opacifying power of various shapes including spherical shapes, oblate shapes either alone or in combinations with two or more of them.

When aqueous color material composition is used as cosmetics, known colorants which are usually compounded for cosmetics can be used. For example, inorganic white pigments such as titanium dioxide and zinc oxide and the like, inorganic reddish pigments such as iron oxide (colcothar), iron titanate and the like, inorganic brownish pigment such as γ iron oxide and the like, inorganic yellowish pigments such as yellow iron oxide and yellow ocher and the like, inorganic blackish pigments such as black iron oxide, carbon black, low-order titanium oxide and the like, inorganic purplish pigments such as mango violet and cobalt violet and the like, inorganic greenish pigments such as chromium oxide, chromium hydroxide, and cobalt titanate, inorganic bluish pigments such as ultramarine blue and iron blue and the like, organic pigments such as mica coated with titanium oxide, bismuth oxychloride coated with titanium oxide, talc coated with titanium oxide, colored mica coated with titanium oxide, bismuth oxychloride, Red 201, Red 202, Red 204, Red 205, Red 220, Red 226, Red 228, Red 405, Orange 203, Orange 204, Yellow 205, Yellow 401, and Blue 404 and the like, organic pigments including zirconium, barium, and aluminum lake such as Red 3, Red 104, Red 106, Red 227, Red 230, Red 401, Red 505, Orange 205, Yellow 4, Yellow 5, and Yellow 202, Yellow 203, Green 3, and Blue 1, natural pigments such as chlorophyll and β-Carorin can exemplified but are not limited to these as far as materials can be used for cosmetics.

It is preferable that the content of a colorant is 0.01 to 20% by weight with respect to the total amount of aqueous color material composition such as an aqueous ink. When the content of said colorant is less than 0.01% by weight with respect to the total amount of said composition, coloring by said colorant is difficult to be visually recognized. When the colorant exceeds 20% by weight with respect to the total amount of said composition, viscosity becomes too high as aqueous color material composition, in particular, as an aqueous ink, and fluidity lowers and furthermore, even in the case of a glittering pigment having a water repellent surface with a median diameter of at least 10 µm, exclusion of a colorant from a glittering pigment particle surface is not enough and glittering property deteriorates.

For information, when the content of a glittering pigment, preferably, when the content of a glittering pigment such as a scaly glittering pigment with a median diameter of at least 10 µm is 0.01 to 40% by weight with respect to the total amount of the aqueous color material composition such as an aqueous ink composition and the like, it is preferable that the content of said colorant is 0.05 to 15% by weight. When the content of said colorant is not less then 0.05% by weight, coloring property (coloring effect) is further improved, and when the content is less than 15% by weight, since satisfactory amount of a colorant gathers around a glittering pigment particle, satisfactory coloring (coloring effect) is obtained.

(Solvent)

In the case of an aqueous color material composition such as an aqueous ink and the like, water, water-soluble organic solvents, and the like can be used as solvents. In particular, it is preferable to use such water-soluble organic solvents as capable of preventing drying at the tip portion of an ink flow of a color material composition in a writing instrument or a coated film such as a pen tip of a ball-point pen and the like and capable of preventing freezing of an aqueous color material composition such as an aqueous ink, and the like.

Examples include alcohols such as methanol, ethanol, and the like, trimethylol propane, glycols such as ethylene glycol, diethylene glycol, triethylene glycol, propylene glycol and polyethylene glycol, polyhydric alcohols such as glycerin, glycol ethers such as ethylene glycol monomethyl ether, diethylene glycol monomethyl ether, dipropylene glycol monomethyl ether and dipropylene glycol monopropyl ether, and the like. For information, as aqueous solvents used in the present invention, water, aliphatic alcohols with carbon number 1 to 4, propylene glycol monomethyl ether, glycerin, and the like are particularly preferable. These solvents may be used alone or in combinations of two or more of them.

It is preferable that the content of the water-soluble organic solvent is 1.00 to 4.0% by weight with respect to the total amount of a color material composition such as an ink composition. When the content of said water-soluble organic solvent is less than 1.00% by weight relative to the total amount of said ink composition, said tip portion of an ink flow such as a pen tip gets susceptible to dry and a color material composition such as an aqueous ink gets liable to freeze. When the content of water-soluble solvent exceeds 40% by weight relative to the total amount of a color material composition such as an aqueous ink and the like, solubility of said water-soluble resin is affected and a written mark or a coated film is hard to dry. Although the optimum content of a solvent, in particular, the optimum content of a water soluble organic solvent somewhat varies depending on kinds of water soluble organic solvents, it is 5.00 to 20% by weight.

(Water-soluble Thickening Resin)

In the present invention, it is preferable to use a water soluble thickening resin as an aqueous material composition capable of adjusting viscosity of an aqueous color material composition such as an aqueous ink and the like as well as preventing dispersion and precipitation of a glittering pigment particle (a scaly glittering particle and the like).

To cite an example of a water-soluble thickening resin, microbial polysaccharides and derivatives thereof are used. For example, pullulan, xanthan gum, welan gum, rhamsan gum, succinoglucan and dextran and the like are exemplified. Also, water-soluble polysaccharides derived from plants and derivatives thereof are used. For example, tragacanth gum, guar gum, tara gum, locust bean gum, ghatti gum, arabinogalactan gum, gum arabic, quince seed gum, pectin, starch, psyllium seed gum, pectin, carrageenan, alginic acid, agar and the like can be exemplified. Also, water-soluble polysaccharides derived from animals and derivatives thereof are used. For example, gelatin, casein and albumin can be exemplified. Moreover, as a thickening resin, N-vinylacetamide type resins such as N-vinylacetamide resin and crosslinked N-vinylacetamide resin can be used. In addition, water-soluble synthetic resin such as acryl, styrene acryl, Na or $NH_4$ salt of styrene maleic acid and the like can be used. Further, water dispersible resin can be used.

In the present invention, in the case of an aqueous color material composition, in particular, in the case of an ink, among said water-soluble thickening resin, in particular, microbial polysaccharides and derivatives thereof, and among them, at least one species of water-soluble thickening resin selected from the group of pullulan, xanthan gum, welan gum, rhamsan gum, and succinoglucan. Further, said water-soluble resin can be used either alone or in combinations of two or more of them.

It is preferable that the content of water-soluble thickening resin is 0.01–10% by weight with respect to the total amount of a color material composition such as an aqueous ink. When the content of said water-soluble resin is less than 0.01% by weight with respect to the total amount of a color material composition such as an aqueous ink and the like, effect on preventing precipitation of a glittering pigment having a water repellent particle surface becomes unsatisfactory. When the content of a water-soluble thickening resin exceeds 10% by weight with respect to the total amount of an aqueous color material composition such as an aqueous ink, viscosity as an aqueous color material composition comprising a glittering pigment having a water repellent particle surface, in particular, as an aqueous ink becomes too high and fluidity deteriorates. Although the optimum content of a water-soluble resin somewhat varies depending on kinds of water-soluble resin, it is 0.1 to 2% by weight.

(Fixing Resin)

Since glittering pigments comprised in an aqueous color material composition of the present invention have a water repellent particle surface, it is preferable to use a fixing resin to fully fix said glittering pigments on a written mark or a coated film. As a fixing resin, synthetic resin emulsion is preferable. Water-soluble polymers generally used for cosmetics such as carboxymethyl cellulose, methyl cellulose, hydroxymethyl cellulose, polyvinyl alcohol, and polyvinyl pyrrolidone are used.

For information, considering the characteristics of a color material composition such as an ink or cosmetics and writing aptitude or coating aptitude, it is important to use a fixing resin that does not affect solubility of resin components of water soluble thickening resin and the like, viscosity of a composition, dispersibility of a colorant, and coloring effect of a color material composition such as an ink. It is also important that a fixing resin does not inhibit effects such as glittering property and the like by compounding a glittering pigment particle including a metal coated glass flake pigment particle.

It is preferable that the minimum film forming temperature of said synthetic resin emulsion is not greater than 20° C. When the minimum film forming temperature of a synthetic resin emulsion is not greater than 20° C., in particular, not greater than 0° C., a film can be formed in cold places not to mention at a normal temperature around (25° C.), thereby capable of enhancing fixing property of a written mark or a coated film to a substrate.

In addition, regarding synthetic resin emulsion, it is preferable to use synthetic resin emulsion having anionic or nonionic property. Synthetic resin emulsion having anionic or nonionic property can be obtained by producing synthetic resin from anionic or nonionic monomer or by using anionic or nonionic emulsifying agent. When synthetic resin emulsion has anionic or nonionic property, stability of aqueous color material composition such as aqueous ink can be enhanced.

Further, such synthetic resin emulsion is preferable that does not affect dispersibility of a colorant or solubility of water soluble thickening resin in which pH of an aqueous color material composition such as an aqueous ink and the like is not less than 6.

From these viewpoints, as synthetic resin emulsion, for example, acryl based synthetic resin emulsions, styrene-acryl based synthetic resin emulsions and vinyl acetate based synthetic resin emulsions can be used. Preferred examples of the acryl based synthetic resins include acryl acid ester copolymer synthetic resin emulsion, alkyl acid ester copolymer resin emulsion, metacryl acid ester copolymer resin emulsion, and metacryl acid alkyl ester copolymer rein emulsion. Preferred examples of the styrene-acryl based synthetic resin emulsion include styrene-acrylate copolymer synthetic resin emulsion and styrene-metacryl copolymer synthetic resin emulsion. As the vinyl acetate based synthetic resin emulsion, vinyl acetate synthetic resin emulsion, vinyl acetate-acrylate ester copolymer synthetic resin emulsion, VeoVa-vinyl acetate copolymer resin emulsion, malate-vinyl acetate copolymer resin emulsion, ethylene-vinyl acetate copolymer resin emulsion for example, are preferably used. Further, others including chlorinated polyolefin, acryl colloidal silica, resin emulsion with special copolymer value can be used. As the synthetic resin emulsion, one species of these synthetic resins can be used and also two or more species of these synthetic resins can lee used in combinations.

For example, the acryl based synthetic resin emulsion can be exemplified by the trade names "Nikasol A-02" (manufactured by Nippon Carbide Industries Co., Inc, minimum film forming temperature=0° C.; viscosity: 500 cps, particle diameter: 0.1 μm), "Nikasol FX-582" (manufactured by Nippon Carbide Industries Co., Inc, minimum film forming temperature=0° C.; viscosity: 500 cps, particle diameter: 0.2 μm), and the like. Further, the vinyl acetate based synthetic emulsion can be exemplified by the trade names "Nikasol TG 134 A" (manufactured by Nippon Carbide Industries Co., Inc.; anionic; pH 7.5; minimum film forming temperature=0° C.), "Mowinyl 507" (manufactured by Clariant Polymers Co., Ltd, nonionic, pH 6.5, minimum film forming temperature=0° C.), and the like.

Although the content of fixing resin such as synthetic resin emulsion is not particularly specified, a preferable range is 0.01—40% by weight in solids with respect to the total amount of the aqueous color material composition such as an aqueous ink. When the content of the fixing resin is not less than 0.01% by weight in solids with respect to the total amount of the aqueous color material composition such as an aqueous ink, fixing property of glittering pigment particles having water repellent property on a particle surface to a written mark or a coated film is enhanced. On the other hand, when the content of said fixing resin exceeds 40% by weight in solids with respect to the total amount of said color material composition, solid resin increases and writing aptitude or coating characteristics deteriorate since coated film is generated at a tip portion of an ink flow such as a pen tip. Further, a written mark or a coated film is liable to whiten. In order to improve fixing property of glittering pigment particles having water repellent property on a particle surface to a written mark or a coated film, it is most suitable that the content of said fixing resin is at least 0.3% by weight in solids with respect to the total amount of the aqueous color material composition. In addition, in order to further improve writing aptitude or coating characteristics, it is most suitable that the content of said fixing resin is 20% by weight in solids with respect to the total amount of said color material composition. In other words, the optimum content of fixing resin such as synthetic resin emulsion is 0.3 to 20% by weight.

(Viscosity of an Aqueous Color Material Composition)

Although the viscosity of an aqueous color material such as an aqueous ink or cosmetics and the like is not specifically limited, it is desirable to be within the viscosity range of 100 to 100000 mPa·s (measured by an ELD viscometer: 3° R14 cone, 0.5 rpm, 20° C.). In particular, an aqueous color material composition such as an aqueous ink having pseudo-plasticity fluidity characteristics (thixotropic property), more preferably, an aqueous color material composition having pseudo-plasticity fluidity characteristics (thixotropic property) in which said thixotropy index (T.I value) is not less than 1.3 which is represented by the ratio of viscosity $V_{0.5}$, the viscosity at a rotation speed of 0.5 rpm to $V_{1.0}$, the viscosity at a rotation speed of 1.0 rpm measured by an ELD viscometer: 3° R14 cone, 20° C. ($V_{0.5}/V_{1.0}$) is preferable.

Further, an aqueous color material composition such as an aqueous ink having pseudo-plasticity fluidity characteristics (thixotropic property) in which $V_{0.5}$, the viscosity at a rotation speed of 0.5 rpm measured by an ELD viscometer: 3° R14 cone, 20° C. is 1000 to 15000 mPa·s is preferable.

In addition, an aqueous color material composition such as an aqueous ink having pseudo-plasticity fluidity characteristics (thixotropic property), in which said thixotropy index (T.I value) is not less than 1.3 which is represented by the ratio of viscosity $V_{0.5}$, the viscosity at a rotation speed of 0.5 rpm to $V_{1.0}$, the viscosity at a rotation speed of 1.0 rpm measured by an ELD viscometer: 3° R14 cone, 20° C. ($V_{0.5}/V_{1.0}$) in which in which $V_{0.5}$, the viscosity at a rotation speed of 0.5 rpm measured by an ELD viscometer: 3° R14 cone, 20° C. is 1000 to 15000 mPa·s is most suitable.

For information, when $V_{0.5}$, the viscosity at a rotation speed of 0.5 rpm measured by an ELD viscometer (3° R14 cone, 20° C.) is less than 1000 m Pa·s, since the viscosity is low in the case of an aqueous color material composition such as an aqueous ink, comprising said glittering pigment particles related to the present invention, dispersal stability deteriorates and sedimentation is liable to occur, which is not preferable. On the other hand, when the viscosity exceeds 15000 mPa·s, since the viscosity is too high, writing performance deteriorates in particular when applied as an ink for ball-point pens.

For information, in the case of a writing instrument having a pen tip made of a fiber bundle, an aqueous color material composition such as an aqueous ink whose viscosity is within the range of 3 to 12 mPa·s (measured by an ELD viscometer: 1° 34' cone, 50 rpm, 20° C.) is preferable.

(Other Additives)

For information, in an aqueous color material composition such as an aqueous ink of the present invention, as required, lubricants such as polyoxyethylene alkali metal salts, dicarboxylic amides, phosphates and N-oleyl sarcosine salts and the like, rust-inhibitors such as benzotriazole and tolyltriazole dicyclohexyl ammonium nitrate and the like, antiseptic mildew-proofing agents such as benzoisothiazoline-type, pentachlorophenol-type and cresol, paraoxybenzoate and the like, surfactants, and a dye dissolving agent can be added.

Further, in an aqueous color material composition of the present invention, bath preparations or moisturizer can be included as well. As said bath preparations or moisturizer, for example, sorbitol, xylitol, glycerine, multitol, propylene glycol, 1,3-butylene glycol, 1,4-butylene glycol, pyrrolidone sodium carboxylate, polyethylene glycol, polyoxyethylene methyl glucoside, panthenol, amino acid, and the like can be exemplified. When using aqueous color material compositions as cosmetics, said bath preparations or moisturizer is particularly preferable.

(Embodiment of Aqueous Glittering Color Material Composition)

From the above, it is preferable that the aqueous glittering color material composition in the present invention is a composition which comprises a colorant, a solvent, and a glittering pigment having a water repellent particle surface and that a median diameter of said glittering pigment particle is at least 10 µm.

In addition, as an aqueous color material composition, a color material composition comprising a glittering pigment which has a particle surface with a water repellent treatment, whose median diameter is at least 10 µm, and which is selected at least one from the group of a metal coated glass flake pigment, metal coated inorganic pigment, and aluminum pigment is preferable.

Further for example, an aqueous color material composition comprising the following component is preferable.

That is, an aqueous glittering color material composition comprises (a) a glittering pigment having a water repellent particle surface and a median diameter of said particle is at least 10 µm and selected at least one from the group of a metal coated glass flake pigment, a metal coated inorganic pigment, and an aluminum pigment and (b) a colorant.

Further, an aqueous glittering color material composition comprising following components is preferable.

(a) a metal coated glass flake pigment as said glittering pigment having a particle surface with water repellent treatment by titanate or silane coupling agent.

(b) a colorant, and (c) a fixing resin.

For information, in the case of a color material composition prefer able for writing instruments such as ball-point pens or marking pens, in particular, in the case of an aqueous ink, an ink composition comprising a colorant such ast a water soluble dye, a water soluble pigment, and a water dispersible pigment, an aqueous solvent such as water and a water-soluble organic solvent, a water soluble thickening resin, a glittering pigment having a water repellent particle surface (in particular, a glittering pigment having a water repellent surface with water repellent treatment by water repellent agents mentioned above) or an ink composition further comprising a fixing agent such as synthetic resin emulsion is preferable. Further, specifically, an aqueous ink composition for writing instruments comprising following components.

(a) a metal coated glass flake having a particle surface with water repellent treatment by a titanate coupling agent or silane coupling agent as a water repellent agent.

(b) a colorant, (c) a water soluble thickening resin (d) a water soluble organic solvent, and (e) water.

Further, specifically, an aqueous color material composition comprising each component (a) to (e) as follows and having the viscosity range of 1000 to 15000 mPa·s (measured by an ELD viscometer: 3° R14 cone, 0.5 rpm, 20° C.) is preferable for a color material composition for writing instrument such as a ball-point pen and a marking pen, in particular for aqueous ink composition.

(a) a glittering pigment selected at least one from the group of a metal coated glass flake, metal coated inorganic pigment, and aluminum pigment and among them, a metal coated glass flake in which a median diameter of a pigment particle is at least 10 µm and whose pigment particle surface is under water repellent treatment by a titanate or silane coupling agent.

(b) a colorant (c) a water soluble thickening resin selected at least one from a group of pullulan, xanthane gum, welan gum, rhamsan gum, and succinoglycan (d) a water soluble organic solvent, and (e) water Further, it is preferable that an aqueous glittering color material composition comprising the following components with respect to the total amount of the aqueous glittering color material composition is preferable.

(a) 0.01 to 40% by weight of a metal coated glass flake pigment as said glittering pigment having a particle surface conducted with water treatment by a titanate or silane coupling agent, (b) 0.05 to 15% by weight of a colorant, and (c) 0.01 to 40% of a fixing resin, For information, as a fixing resin which fixes a glittering pigment of the present invention to a written mark or a coated film, as already mentioned, at least one fixing resin selected from a group of synthetic resin emulsion, carboxymethyl cellulose, methyl cellulose, hydroxymethyl cellulose, polyvinyl aocohol, and polyvinyl pyrrolidone can preferably be used.

Said color material composition in each kind of embodiments can particularly be used for an ink for writing instruments, each kind of cosmetics including body paints or inks which coat on a face, arms, or the like, preferably.

(Use Application)

The above mentioned aqueous color material composition can be used for inks such as inks for ballpoint pens, inks for marking pens, stamp inks, stencil inks, in particular, the present composition can be used for writing instruments such as ball-point pens and marking pens. In particular, the present composition can preferably be used for a writing instrument whose ink containment portion is a hollow cylinder tube or a central core made of a fiber bundle and a writing instrument in which a pen tip is composed of a ball or a fiber bundle. In addition, the composition of the present invention can be widely applied as an aqueous color material composition comprising a colorant, a solvent, and a water repellent particle surface, in particular, a water repellent particle surface which rejects said colorant.

Other than applications for paints or coating materials which comprise these color materials, the present invention can be applied for cosmetics, in particular, for make-up cosmetics which coat particularly on a surface of skins, of hairs, and of nails. In other words, a color material composition of the present invention can be applied as cosmetics, paints, stamp inks, and stencil inks, respectively, as well as to be applied for an ink for ball-point pens and an ink for marking pens.

For information, when this color material composition is applied as cosmetics, it can be applied as transfer type cosmetics in which the composition is transferred to skins and the like. Also, it can be applied as an applicator of a ball-point pen type (a ball-point pen type container) in which a ball is retained at a pen tip and cosmetics filled in a contained are coated on a surface of skins or of nails with a rotation of said ball. In this case, liquid cosmetics or semi-liquid cosmetics such as emulsion cosmetics can be filled in a containment portion in a container. However, it is also possible to apply it as an applicator of a ball-point pen type (a ball-point pen type container) which has not been found in the past, in which a shear force acts on cosmetic composition with a rotation of a ball, decreasing viscosity and liquidating, thereby coating on a surface of skins, of hairs, or of nails although it is a highly viscous gel type (nonliquid or hard flow) cosmetic composition in said applicator. In addition, regarding a tip, it can be applied not only for a ball-point pen tip, but also for a pen type applicator (pen-type container) which is composed of a fiber bundle and for a container having a structure in which a tip portion where cosmetic liquid of a color material composition flows out is made of fibers, brushes, felts, sponges, and similar things thereof and flow is made by pressurizing or not pressurizing a color material composition filled in a container by pushing out from pores of said container along with said fibers and the like. Further, it can be applied not only for a direct liquid supply structure but also for a central core type in which cosmetics are impregnated in a central core such as fiber bundles and for a valve type applicator (pen type container) in which supply is made at a tip portion of a flow of a pen tip via a valve.

A color material composition of the present invention can be used as cosmetics such as facial cosmetics, make-up cosmetics, and hair cosmetics. In particular, it can preferably be used not only as manicures, pedicures, nail polishes, mascaras, eye liners, eye shadows, lip sticks, cheeks, foundations, but also as paints or inks for writing or coating on bodies such as a face, hands, arms, and the like.

EXAMPLES (Preparation of a Water Repellent Glittering Pigment)

Each kind of water repellent glittering pigments A to G whose surface was made water repellent by a water repellent agent was prepared with a composition as shown in Table 1. To be specific, when coupling agents were used as water repellent agents, 10 g of a glittering pigment and 0.5 g of a coupling agent are added to 100 g of water when a coupling agent dissolves in water, and 100 g of a solvent (n-hexane, for example) when a coupling agent does not dissolve in water, followed by shaking up well for 30 minutes. The liquid mixture is filtered, bringing out a glittering pigment, followed by heating (about 4 hours at 80° C.) thereby drying. For information, for comparison, non water repellent glittering pigments H and I without water repellent treatment were shown in Table 1.

TABLE 1

|  |  | Glittering pigment with water repellent treatment | | | | | | Glittering pig. without water repellent treatment (g) | |
| --- | --- | --- | --- | --- | --- | --- | --- | --- | --- |
|  |  | A | B | C | D | E | F | G | H | I |
| Glittering pigment | I | 10.0 | 10.0 | 10.0 | 10.0 | 10.0 | 10.0 |  | 10.0 |  |
|  | II |  |  |  |  |  |  | 10.0 |  | 10.0 |
| Water repellent agent | I | 0.5 |  |  |  |  |  |  |  |  |
|  | II |  | 0.5 |  |  |  |  |  |  |  |
|  | III |  |  | 0.5 |  |  |  |  |  |  |
|  | IV |  |  |  | 0.5 |  |  |  |  |  |
|  | V |  |  |  |  | 0.5 |  | 0.5 |  |  |
|  | VI |  |  |  |  |  | 0.5 |  |  |  |
| Water |  | 100.0 | 100.0 |  |  |  | 100.0 |  |  |  |
| N-hexane |  |  |  | 100.0 | 100.0 | 100.0 |  | 100.0 |  |  |

(Preparation of an Ink)

With a composition and compounding amount (weight %) as shown in Table 2, water, an organic solvent, each water repellent glittering pigment of A to G (or each non water repellent glittering pigment H and I) were mixed and a water soluble thickening resin was added to a well dispersed solution followed by stirring further and after dispersing other additives, pH was adjusted as required, followed by adding a colorant, thereby obtaining an ink. In both Examples and Comparative Examples, heretofore known method was adopted as dispersing method, defoaming method, filtering and the like.

(Preparation of a Test Sample)

An aqueous ink for ball-point pens obtained by the above mentioned method was filled in an ink container of a ball point pen composed of a hollow cylinder tube made of a polypropylene provided with a stainless ball-point pen tip (a material of a ball: silicon carbide) at one end, thereby preparing a test sample. A diameter of a ball is 1.00 mm.

[Evaluation]

A written mark written on PPC paper was photographed by a microscope, binarizing image data processing based on a gray scale on the computer, thereby calculating a ratio of a colorant (%) which coats on a glittering pigment. The small value shows higher effect of water repellency since the amount of a colorant coating on a glittering pigment. Glittering property was visually observed and the results were shown by ⊚ for very good, ○ for good, and X for bad.

TABLE 2

| | | Example | | | | | | | | | Comparative Example (% by weight) | |
|---|---|---|---|---|---|---|---|---|---|---|---|---|
| | | 1 | 2 | 3 | 4 | 5 | 6 | 7 | 8 | 9 | 1 | 2 |
| Glittering pigment with water repellent treatment | A | 4.0 | | | | | | | | | | |
| | B | | 4.0 | | | | | | | | | |
| | C | | | 4.0 | | | | | | | | |
| | D | | | | 4.0 | | | | | | | |
| | E | | | | | 4.0 | | | 4.0 | 4.0 | | |
| | F | | | | | | 4.0 | | | | | |
| | G | | | | | | | 4.0 | | | | |
| Glittering pigment without water repellent treatment | H | | | | | | | | | | 4.0 | |
| | I | | | | | | | | | | | 4.0 |
| Fixing resin | I | | | | | | | | 5.0 | | | |
| | II | | | | | | | | | 5.0 | | |
| Water soluble. thickening resin | I | 0.3 | 0.8 | 0.3 | 0.3 | 0.8 | 0.3 | 0.3 | 0.8 | 0.3 | 0.3 | 0.3 |
| | II | 0.2 | 0.2 | 0.2 | 0.2 | 0.2 | 0.2 | 0.2 | 0.2 | 0.2 | 0.2 | 0.2 |
| Water soluble org. solvent | I | 8.0 | 8.0 | 8.0 | 8.0 | 8.0 | 8.0 | 8.0 | 8.0 | 8.0 | 8.0 | 8.0 |
| Colorant | I | 8.0 | 8.0 | 8.0 | 8.0 | 8.0 | 8.0 | 8.0 | 8.0 | 8.0 | 8.0 | 8.0 |
| Antiseptic agent | I | 0.4 | 0.4 | 0.4 | 0.4 | 0.4 | 0.4 | 0.4 | 0.4 | 0.4 | 0.4 | 0.4 |
| Lubricant | I | 1.5 | 1.5 | 1.5 | 1.5 | 1.5 | 1.5 | 1.5 | 1.5 | 1.5 | 1.5 | 1.5 |
| Water | | 77.6 | 77.6 | 77.6 | 77.6 | 77.6 | 77.6 | 77.6 | 72.6 | 72.6 | 77.6 | 77.6 |
| Total | | 100.0 | 100.0 | 100.0 | 100.0 | 100.0 | 100.0 | 100.0 | 100.0 | 100.0 | 100.0 | 100.0 |
| Covering ratio of a colorant (%) | | 22 | 22 | 18 | 22 | 16 | 18 | 17 | 18 | 20 | 89 | 90 |
| Glittering property | | ○ | ○ | ○ | ○ | ◎ | ○ | ◎ | ○ | ○ | X | X |

For information, in each table, each component is as follows.

[Glass Flake Pigment]
I Trade name "Metashine REFSX-2040PS", manufactured by Toyo Aluminium Co., Ltd.
II Trade name "Metashine RCFSX-1040RC (9546) Red", manufactured by Toyo Aluminium Co., Ltd.

[Water Repellent Agent]
I Trade name "KR ET", manufactured by Ajinomoto Fine Techno Co Inc., titanate coupling agent
II Trade name "KR 44", manufactured by Ajinomoto Fine Techno Co Inc., titanate coupling agent
III Trade name "KR TTS", manufactured by Ajinomoto Fine Techno Co Inc., titanate coupling agent
IV Trade name "KR 38S", manufactured by Ajinomoto Fine Techno Co Inc., titanate coupling agent
V Trade name "KR 138", manufactured by Ajinomoto Fine Techno Co Inc., titanate coupling agent
VI Trade name "KBM 403", manufactured by Shin-Etsu Chemical Co. Ltd, silane coupling agent

[Fixing Resin]
I Trade name "Nikasol A ·02" (manufactured by Nippon Carbide Industries Co., Inc, MFT=0° C., pH: 7.0, viscosity: 500 cps, average particle diameter: 0.1μ)
II Trade name "Nikasol FX-582 special order" manufactured by Nippon Carbide Industries Co., Inc, MFT=0° C., pH: 7.0, viscosity: 500 cps, average particle diameter: 0.2μ)

[Thickening Resin]
I Xanthane gum trade name "Kelzan" manufactured by CP Kelco ApS
II Polyacrylic acid: trade name "Carbopol 940" manufactured by BF Goodrich Co., Ltd.

[Water Soluble Organic Solvent]
I Glycerine: reagent
II Propylene glycol: reagent

[Colorant]
I Blue pigment dispersion:
A pigment dispersion with an average particle size of 0.08 un and with a solid content of 10% by concentration was obtained by adding NaOH to a colorant of following ratio (parts by weight) and by dissolving, followed by dispersing with a bell mill. The following styrene-acryl copolymer is a resin for pigment dispersion with a trade name of "JOHNCRYL J683", manufactured by Johnson Polymer Co., Ltd., with a weight average molecular weight of 8000.

| Phthalocyanine blue | 5 parts by weight |
|---|---|
| Styrene-acryl copolymer | 1 part by weight |

[Antiseptic Mildew-Proofing Agent]
I 1,2-Benzoisothiazolin-3-on: trade name "Proxel XL-2" manufactured by Hoechst synthesis Co., Ltd.

[Lubricant]
I Mono (or di) polyoxyethylene alkyl ether phosphoric acid: trade name "Phosphanol PE-510" manufactured by Toho Chemical Industry Co, Ltd.

From table 2, while coverage ratio of a colorant was around 90% in Comparative Examples 1 and 2 without water repellent treatment, it was recognized that coverage ratio of a colorant in every Example was not greater than 22%, in detail, 16 to 22% and in view of visual observation, glittering property was found to be improved in accordance with coverage ratio of this colorant. Further, particularly, in Examples 8 and 9 in which a fixing agent was included, fixing property was also improved.

INDUSTRIAL APPLICABILITY

As mentioned above, since the present invention relates to a glittering color material composition comprising a glittering pigment having a water repellent particle surface, in particular, a particle surface with a water repellent treatment, compared to a composition comprising a glittering pigment having no water repellent particle surface, the present invention can have a written mark or a coated film provided both with improved coloring effect by a colorant and improved glittering property by a glittering pigment. Therefore the present invention can be applied for an ink for writing instruments, a marking ink, paints, a stamp ink, a stencil ink, coating materials, as well as for cosmetics, in particular, for make-up cosmetics.

What is claimed is:

1. An aqueous glittering color material composition comprising:
   a colorant;
   a solvent; and
   glittering pigments,
   wherein said glittering include metal reflection surfaces on particle surfaces of said pigments or inside particles of said pigments, and said metal reflection surfaces having water repellent particle surfaces.

2. An aqueous glittering color material composition as set forth in claim 1, wherein a median diameter of said glittering pigment particles is at least 10 μm.

3. An aqueous glittering color material composition as set forth in claim 1, wherein said glittering pigment is a glass flake pigment with a structure in which a glass flake is coated with a metal.

4. An aqueous glittering color material composition as set forth in claim 1, wherein a surface of said particles is a particle surface with water repellent treatment.

5. An aqueous glittering color material composition as set forth in claim 4, wherein a surface of said particles is subject to water repellent treatment by a water repellent agent.

6. An aqueous glittering color material composition as set forth in claim 5, wherein said water repellent agent is a coupling agent.

7. An aqueous glittering color material composition as set forth in claim 6, wherein said coupling agent is a titanate or a silane coupling agent.

8. An aqueous glittering color material composition as set forth in claim 3, wherein a pigment particle surface of said metal coated glass flake pigment is a particle surface with a water repellent treatment.

9. An aqueous glittering color material composition as set forth in claim 8, wherein a pigment particle surface of said metal coated glass flake pigment is a particle surface with a water repellent treatment with a water repellent agent.

10. An aqueous glittering color material composition as set forth in claim 9, wherein said water repellent agent is a coupling agent.

11. An aqueous glittering color material composition as set forth in claim 10, wherein said coupling agent is a titanate or a silane coupling agent.

12. An aqueous glittering color material composition as set forth in claim 1, further wherein the glittering pigment comprising a colorant and a solvent and having said water repellent particle surfaces is a glittering pigment which resists said colorant.

13. An aqueous glittering color material composition as set forth in claim 12, further comprising a fixing resin.

14. An aqueous glittering color material composition as set forth in claim 1, comprising 0.01 to 40% by weight of said glittering pigment having said water repellent particle surface and 0.05 to 15% by weight of said colorant with respect to the total amount of the aqueous glittering color material composition.

15. An aqueous glittering color material composition as set forth in claim 5, wherein said water repellent agent is contained at least in 0.1% by weight with respect to the total amount of a glittering pigment.

16. An aqueous glittering color material composition as set forth in claim 13, wherein said fixing resin is contained in 0.01 to 40% by weight with respect to the total amount of the aqueous glittering color material composition.

17. An aqueous glittering color material composition as set forth in claim 1, wherein a color material composition has the viscosity range of 100 to 100000 mPa·s (measured by an ELD viscometer 3°, R 14 cone, 0.5 rpm, at a temperature of 200° C.).

18. An aqueous glittering color material composition as set forth in claim 1, comprising the following components with respect to the total amount of the aqueous glittering color material composition;
   (a) 0.01 to 40% by weight of a metal coated glass flake pigment as said glittering pigment having a particle surface with water repellent treatment by a titanate or silane coupling agent,
   (b) 0.05 to 15% by weight of a colorant, and
   (c) 0.01 to 40% by weight of a fixing resin.

19. An aqueous glittering color material composition as set forth in claim 1, wherein the color material composition is an ink composition.

20. An aqueous glittering color material composition for writing instruments as set forth in claim 19, comprising the following components;
   (a) a metal coated glass flake pigment having a particle surface with water repellent treatment by a titanate or silane coupling agent as a water repellent agent,
   (b) a colorant,
   (c) a water soluble thickening resin,
   (d) a water soluble organic solvent, and
   (e) water.

21. An aqueous ink composition for ball-point pens as set forth in claim 20, wherein an ink has a viscosity range of 1000 to 15000 mPa·s (measured by an ELD viscometer 3°, R 14 cone, 0.5 rpm, at a temperature of 200° C.).

22. An aqueous ink composition for writing instruments having a pen tip made of a fiber bundle as set forth in claim 20, wherein an ink has a viscosity range of 3 to 12 mPas (measured by an ELD viscometer 1°, 34' cone, 50 rpm, at a temperature of 20° C.).

23. A writing instrument wherein an ink comprising a glittering pigment having a particle surface with a water repellent treatment, and the ink is contained in an ink containment portion.

24. A writing instrument as set forth in claim 23, wherein the ink containment portion is a central core of a hollow cylinder tube or of a fiber bundle and a pen tip is composed of a ball or a fiber bundle.

25. A writing instrument as set forth in claim 23, wherein an ink with a viscosity range of 1000 to 15000 mPa·s (measured by an ELD viscometer 3°, R 14 cone, 0.5 rpm, at a temperature of 20° C.) comprising the following components (a) to (e);
   (a) a metal coated glass flake pigment in which a median diameter of a pigment particle is at least 10 μm and is subject to water repellent treatment by a titanate or silane coupling agent,
   (b) a colorant,
   (c) a water soluble thickening resin selected at least one from a group of pulullan, xanthane gum, welan gum, rhamsan gum, and succinoglycan,
   (d) a water soluble orgaoic solvent, and
   (e) water.

26. An aqueous glittering color material composition as set forth in claim 1, wherein a color material composition is a cosmetic.

27. An aqueous glittering color material composition as set forth in claim 1, wherein a color material composition is a paint.

28. An aqueous glittering color material composition as set forth in claim 1, wherein a color material composition is a stamp ink.

29. An aqueous glittering color material composition as set forth in claim 1, wherein a color material composition is a stencil ink.

30. An aqueous glittering color material composition as set forth in claim 1, wherein a color material composition is a coating material.

31. A metal coated glass flake pigment, comprising: a pigment particle surface having a water repellent treatment with a water repellent agent.

32. A metal coated glass flake pigment as set forth in claim 31, wherein said water repellent agent is a coupling agent.

33. A metal coated glass flake pigment as set forth in claim 32, wherein said coupling agent is a titanate or a silane coupling agent.

* * * * *